(12) United States Patent
Perea Rodriquez et al.

(10) Patent No.: US 7,947,287 B2
(45) Date of Patent: *May 24, 2011

(54) PEPTIDES FOR THE TREATMENT OF CANCER ASSOCIATED WITH THE HUMAN PAPILLOMA VIRUS (HPV) AND OTHER EPITHELIAL TUMORS

(75) Inventors: Silvio Ernesto Perea Rodriquez, Ciudad de la Habana (CU); Osvaldo Reyes Acosta, Ciudad de la Habana (CU); Nelson Francisco Santiago Vispo, Ciudad de la Habana (CU); Yaquelin Puchades Izaguirre, Ciudad de la Habana (CU); Ricardo Silva Rodriguez, Ciudad de la Habana (CU); Alejandro Moro Soria, Ciudad de la Habana (CU); Alicia Santos Savio, Ciudad de la Habana (CU); Luis Javier Gonzalez Lopez, Ciudad de la Habana (CU); Belkis Gonzalez Barrios, Ciudad de la Habana (CU)

(73) Assignee: Centro de Ingenieria Genetica y Biotecnolgia, Ciudad de La Habana (CU)

( * ) Notice: Subject to any disclaimer, the term of this patent is extended or adjusted under 35 U.S.C. 154(b) by 236 days.

This patent is subject to a terminal disclaimer.

(21) Appl. No.: 12/099,646

(22) Filed: Apr. 8, 2008

(65) Prior Publication Data

US 2009/0005294 A1    Jan. 1, 2009

Related U.S. Application Data

(63) Continuation-in-part of application No. 10/499,458, filed as application No. PCT/CU02/00010 on Dec. 4, 2002, now Pat. No. 7,374,767.

(30) Foreign Application Priority Data

Dec. 20, 2001 (CU) .................................. 0309/01

(51) Int. Cl.
*A61K 39/12* (2006.01)
(52) U.S. Cl. .................................................. 424/204.1
(58) Field of Classification Search .................. None
See application file for complete search history.

(56) References Cited

U.S. PATENT DOCUMENTS 7,374,767 B2 * 5/2008 Perea Rodriguez et al. .......................... 424/204.1

FOREIGN PATENT DOCUMENTS

WO   WO 01/64835   * 9/2001

* cited by examiner

*Primary Examiner* — Ali R. Salimi
(74) *Attorney, Agent, or Firm* — Hoffman & Baron, LLP

(57) ABSTRACT

This invention is related to the Molecular Pharmacology field and especially to the development of peptides useful for treating epithelial tumors and mainly those associated to oncogenic types of HPVs. The main objective of this invention is to identify peptides whose structure permits to block the Casein Kinase II (CKII) phosphorylation domain by direct interaction with such a site. In the present invention it is shown eleven cyclic peptides with different aminoacid sequences which inhibit the CKII phosphorylation in vitro, exhibit cytotoxicity on HPV-16 transformed cells (CaSki) and also increase the sensitivity of these cells to the cytostatic effect of interferon (IFN). Furthermore, the invention relates to the use of these peptides conjugated or fused to other peptides and chemical compounds which penetrates into cells as well as with the use of both peptide and chemical mimetic molecules.

3 Claims, 9 Drawing Sheets

SEQUENCE LISTING

<160> NUMBER OF SEQ ID NOS: 68

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 1

Cys Ser Val Arg Gln Gly Pro Val Gln Lys Cys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Cys Ser Ser Cys Gln Asn Ser Pro Ala Leu Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Cys Gln Ile Pro Gln Arg Thr Ala Thr Arg Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Cys Ala Lys Gln Arg Thr Asp Pro Gly Tyr Cys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 5

Cys Trp Met Ser Pro Arg His Leu Gly Thr Cys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Cys Arg Asn Cys Thr Val Ile Gln Phe Ser Cys

```
<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 7

Cys His Tyr Ile Ala Gly Thr Val Gln Gly Cys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Cys Pro Leu Val Ser Leu Arg Asp His Ser Cys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Cys Lys Gln Ser Tyr Leu His His Leu Leu Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 10

Cys Phe Gln Pro Leu Thr Pro Leu Cys Arg Cys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 11

Cys Gln Ser Tyr His Glu Leu Leu Leu Gln Cys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 12

Arg Arg Arg Glu Glu Glu Thr Glu Glu Glu
1               5                   10
```

```
<210> SEQ ID NO 13
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 13

Gly Arg Lys Lys Arg Arg Gln Arg Arg Pro Pro Gln Cys
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Lys Lys Lys Arg Lys Val Glu
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 15

Met Ser Pro Arg His
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 16

Tyr Ile Ala Gly Thr
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 17

Gln Pro Leu Thr Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 18

Leu Ser Pro Arg His
1               5

<210> SEQ ID NO 19
```

```
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 19

Ile Ser Pro Arg His
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 20

Val Ser Pro Arg His
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 21

Cys Ser Pro Arg His
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 22

Met Ala Pro Arg His
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 23

Met Thr Pro Arg His
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 24

Met Pro Pro Arg His
1               5

<210> SEQ ID NO 25
<211> LENGTH: 5
<212> TYPE: PRT
```

```
<213> ORGANISM: Artificial Sequence
<220> FEATURE:
<223> OTHER INFORMATION: Synthetic Peptide

<400> SEQUENCE: 25

Met Gly Pro Arg His
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 26

Met Ser Ala Arg His
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Met Ser Ser Arg His
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 28

Met Ser Thr Arg His
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 29

Met Ser Gly Arg His
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 30

Met Ser Pro His His
1               5

<210> SEQ ID NO 31
<211> LENGTH: 5
<212> TYPE: PRT
<213> ORGANISM: Artificial Sequence
<220> FEATURE:
```

```
<223> OTHER INFORMATION: Synthetic Peptide

<400> SEQUENCE: 31

Met Ser Pro Lys His
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 32

Met Ser Pro Arg Phe
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 33

Met Ser Pro Arg Tyr
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 34

Met Ser Pro Arg Trp
1               5

<210> SEQ ID NO 35
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 35

Gly Thr Ala Ser Ala Ala Gly Ala Ala Gly Gly Ala Tyr Ala Ala Gly
1               5                   10                  15

Ser His Ile Gly Ala
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 36

Gly Thr Ala Ser Ala Ala Gly Ala Ala Gly Gly Ala Tyr Ala Ala Gly
1               5                   10                  15

Ser His Ile Gly
            20

<210> SEQ ID NO 37
```

```
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 37

Gly Thr Ala Ser Ala Ala Gly Ala Ala Gly Gly Ala Tyr Ala Ala Gly
1               5                   10                  15

Ser His Ile Cys
            20

<210> SEQ ID NO 38
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 38

Gly Thr Ala Ser Ala Ala Gly Ala Ala Gly Gly Ala Tyr Ala Ala Gly
1               5                   10                  15

Ser His Ile

<210> SEQ ID NO 39
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 39

Gly Thr Ala Ser Ala Ala Gly Ala Ala Gly Gly Ala Tyr Ala Ala Gly
1               5                   10                  15

Ser His

<210> SEQ ID NO 40
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 40

Gly Thr Ala Ser Ala Ala Gly Ala Ala Gly Gly Ala Tyr Ala Ala Gly
1               5                   10                  15

Ser

<210> SEQ ID NO 41
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 41

Gly Thr Ala Ser Ala Ala Gly Ala Ala Gly Gly Ala Tyr Ala Ala Gly
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic Peptide
```

```
<400> SEQUENCE: 42

Gly Thr Ala Ser Ala Ala Gly Ala Ala Gly Gly Ala Tyr Ala Ala
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 43

Gly Thr Ala Ser Ala Ala Gly Ala Ala Gly Gly Ala Tyr Ala
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 44

Gly Thr Ala Ser Ala Ala Gly Ala Ala Gly Gly Ala Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 45

Gly Thr Ala Ser Ala Ala Gly Ala Ala Gly Gly Ala
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 46

Gly Thr Ala Ser Ala Ala Gly Ala Ala Gly Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 47

Gly Thr Ala Ser Ala Ala Gly Ala Ala Gly
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 48
```

```
Gly Thr Ala Ser Ala Ala Gly Ala Ala
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 49

Gly Thr Ala Ser Ala Ala Gly Ala
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 50

Gly Thr Ala Ser Ala Ala Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 51

Gly Thr Ala Ser Ala Ala
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 52

Gly Thr Ala Ser Ala
1               5

<210> SEQ ID NO 53
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 53

Gly Thr Ala Ser
1

<210> SEQ ID NO 54
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 54

Cys Ala Met Ser Pro Arg His Leu Gly Thr Cys
1               5                   10
```

```
<210> SEQ ID NO 55
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 55

Cys Trp Ala Ser Pro Arg His Leu Gly Thr Cys
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 56

Cys Trp Met Ala Pro Arg His Leu Gly Thr Cys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 57

Cys Trp Met Ser Ala Arg His Leu Gly Thr Cys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 58

Cys Trp Met Ser Pro Ala His Leu Gly Thr Cys
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 59

Cys Trp Met Ser Pro Arg Ala Leu Gly Thr Cys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 60

Cys Trp Met Ser Pro Arg His Ala Gly Thr Cys
1               5                   10
```

```
<210> SEQ ID NO 61
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 61

Cys Trp Met Ser Pro Arg His Leu Ala Thr Cys
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 62

Cys Trp Met Ser Pro Arg His Leu Gly Ala Cys
1               5                   10

<210> SEQ ID NO 63
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 63

Cys Ala Gly Trp Met Ala Pro Arg His Leu Gly Thr Ala Ser Ala Ala
1               5                   10                  15

Gly Ala Ala Gly Gly Ala Tyr Ala Ala Gly Ser His Ile Gly Ala Cys
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 64

Cys Ala Gly Trp Met Ala Pro Arg His Leu Gly Thr Ala Ser Ala Ala
1               5                   10                  15

Gly Ala Ala Gly Gly Ala Tyr Ala Ala Gly Ser His Ile Cys
            20                  25                  30

<210> SEQ ID NO 65
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 65

Cys Ala Gly Trp Met Ala Pro Arg His Leu Gly Thr Ala Ser Ala Ala
1               5                   10                  15

Gly Ala Ala Gly Gly Ala Tyr Ala Ala Gly Ser His Ile Gly Ala Ala
            20                  25                  30

Cys

<210> SEQ ID NO 66
<211> LENGTH: 32
<212> TYPE: PRT
<213> ORGANISM: Artificial Sequence
```

```
<220> FEATURE:
<223> OTHER INFORMATION: Synthetic Peptide

<400> SEQUENCE: 66

Cys Ala Gly Trp Met Ala Pro Arg His Ala Gly Thr Ala Ser Ala Ala
1               5                   10                  15

Gly Ala Ala Gly Gly Ala Tyr Ala Ala Gly Ser His Ile Gly Ala Cys
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 67

Cys Ala Gly Ala Met Ala Pro Arg His Leu Gly Thr Ala Ser Ala Ala
1               5                   10                  15

Gly Ala Ala Gly Gly Ala Tyr Ala Ala Gly Ser His Ile Gly Ala Cys
            20                  25                  30

<210> SEQ ID NO 68
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 68

Ser Ser Pro Arg His
1               5
```

PEPTIDES FOR THE TREATMENT OF CANCER ASSOCIATED WITH THE HUMAN PAPILLOMA VIRUS (HPV) AND OTHER EPITHELIAL TUMORS

The present application is a Continuation-in-Part of U.S. application Ser. No. 10/499,458, filed on Feb. 22, 2005, now U.S. Pat. No. 7,374,767, which is the U.S. National Phase of International Application Number PCT/CU02/00010, filed on 4 Dec. 2002. The present application also asserts priority to Cuban Application No. CUBA 0309/01 filed on Dec. 20, 2001. The foregoing applications are hereby incorporated by reference herein.

This invention is related to the Molecular Pharmacology field and especially to the development of peptides useful for treating epithelial tumors and mainly those associated to oncogenic types of HPVs. The main objective of this invention is to identify peptides whose structure permits to block the Casein Kinase II (CKII) phosphorylation domain by direct interaction with such a site. In the present invention it is shown eleven cyclic peptides with different aminoacid sequences which inhibit the CKII phosphorylation in vitro, exhibit cytotoxicity on HPV-16 transformed cells (CaSki) and also increase the sensitivity of these cells to the cytostatic effect of interferon (IFN). Furthermore, the invention relates to the use of these peptides conjugated or fused to other peptides and chemical compounds which penetrates into cells as well as with the use of both peptide and chemical mimetic molecules.

BACKGROUND OF THE INVENTION

This invention is related to the Molecular Pharmacology field and especially to the development of peptides useful for treating HPV-associated epithelial tumors as it permits the blocking of the Casein Kinase II (CKII) phosphorylation domain by direct interaction with such a site.

The CKII is a threonine/Serine enzyme involved in the cellular proliferation and its intracellular localization is mainly into nucleus during malignant transformation process (Tawfic S, Yu S, Wang H, Faust R, Davis A, Ahmed K, 2001, Histol. Histopathol. 16:573-582).

Based on the findings reporting CKII high levels in different epithelial solid tumors, it has been assumed that phosphorylation elicited by this enzyme is an important event in malignant transformation and a tumor progression marker (Seldin D C, Leder P, 1995, Science 267:894-897) (Faust R A, Gapany M, Tristani P, Davis A, Adams G L, Ahmed K, 1996, Cancer Letters 101:31-35). On the other hand, the CKII over expression in transgenic mice leads to the tumorigenesis in the mammary glands by increasing the Wnt/beta-catenine signal transduction pathways on these mammary epithelial cells (Landesman-Bollag E, Romien-Mourez R, Song D H, Sonenshein G E, Cardiff R D, Seldin D C, 2001, Oncogene 20:3247-3257).

Among epithelial tumors, those originated by HPVs represent a great fraction. For instant, most of the genitourinary tumors are associated to these oncoviruses and the presence of HPV DNA sequences has been demonstrated in 99.7% of the tumors coming from squamous cervical cells (Walboormers J M, Jacobs M V, Manos M M, Bosch F X, Kummer J A, Shah K V, Snijders P J, Peto J, Meijer C J, Muñoz N, 1999, J. Pathol 189:12-19). Likewise, the WHO has reported about 500 000 cervical cancer patients annually worldwide (Parkin D M, Laara E, Muir C S, 1980, Int. J. Cancer 41:184-1972). In Cuba, 370 women with cervical cancer die annually due to this disease (Organizacion Panamericana de la Salud, 1999, Basic Country Health Profiles for the Americas. Cuba, 206-219)

HPVs are classified in oncogenic and not oncogenic according to whether the lesions progress toward malignancy or not (Lorincz A T, Temple G F, Kurman R J, Jenson A B, Lancaster W D, 1987, J. Natl. Cancer Inst. 79:671-677). HPV-16 and -18 are associated to intraepithelial neoplasia that generally progress toward malignancy and also both HPV types are associated to more than 90% of the dysplasias and cervical carcinomas (Fujinaga Y, Shimada M, Okasawa K, Fukushima M, Kato I, Fujinaga K, 1991 J. Gen. Virol 72:1039-1044).

As no therapeutic or prophylactic vaccine is still available for eradication of HPV-associated tumors, the employment of inhibitors targeting viral transcription and viral oncoproteins, become more attractive. Biomodulators like IFNs have been used with some efficacy in certain HPV-associated diseases like condyloma, plantar warts, and respiratory papillomatosis (Koromilas A E, Li S, Matlashewski G, 2001. Cytokine & Growth Factor Reviews 12:157-170). In previous experiments on HPV-transformed cells (HeLa), we have demonstrated that continuous exposition with IFN alpha produces a reversion of the malignant phenotype of these cells with the concomitant inhibition of the HPV mRNA expression (López-Ocejo O, Perea S E, Reyes A, Vigoa L, López-Saura P, 1993. J. IFN Res 13:369-375). In the same cellular model, we found that IFN alpha modulates the HPV mRNA through the repression of endogenous viral transcription (Perea S E, López-Ocejo O, García-Milián R, Araña M J, 1995, J. IFN & Cytokine Res 15:495-501). In agreement with the results obtained in cell lines, we observed that IFN alpha treatment modulated the mRNA expression in a pilot study in cervical cancer patients (García-Milián R, Rios M A, Díaz D, Silveira M, Guilar O, Amigó M, Araña M J, Perea S E, 1996, J. IFN and Cytokine Res 16:709-713). In spite of the promissory findings about the use of IFN as regulator of the HPV mRNA expression, mounting data indicate a variable IFN response and the resistance phenomenon toward this cytokine has been reported between the 40 and 50% of the patients during clinical trials (Arany I, Tyring S K, Stanley M A, Tomai M A, Miller R L, Smith M H, McDermott, D J, Slade H B, 1999, Antiviral Res 43:55-63). Some molecular and clinical evidences indicate that E7 oncoprotein plays a central role on the IFN-resistance phenomenon. For example, it has been reported that E7 binds to the IFN-induced transcription factor (p48) thus affecting the IFN response by blocking the transcriptional activation (Barnard P and McMillan N A J, 1999, Virology 259:305-313). Furthermore, the alteration of the IFN regulatory factor (IRF-1) in the presence of E7 has been also reported (Park J S, Kim E J, Kwon H J, Hwang E S, Namkoong S E, Um S J, 2000, J Biol Chem 275:6764-6769) (Perea S E, Massimi P, Banks L, 2000, J Mol Med 5:661-666). In clinical trials, the IFN response has been regarded to be depending on the E7 expression in the HPV-containing lesions (Frazer I H, McMillan N A J, 1997, Papillomatosis and condyloma acuminate. Clinical Applications of the Interferons (R Stuart Harris and R D Penny, eds) Pp 79-90. Chapman and Hall Medical, London). The E7 oncoprotein plays an essential role on the malignant transformation elicited by these oncogenic viruses. Thus, it has been demonstrated that E7-induced immortalization of primary cells leads to mutations and chromosomal aberrations since the beginning of the immortalization process (Mougin C, Humbey O, Gay C, Riethmuller D, 2000, J. Gynecol Obstet. Biol. Reprod 29:13-20). On the other hand, we have demonstrated that stable transfection with the E7 gene leads to the development of a IFN-resistant phenotype on sensitive tumor cells (Moro A, Calixto A, Suárez E, Araña M J, Perea S E, 1998, Bioch Bioph Res Comm 245:752-756). Likewise, it has been reported that E7 oncoprotein binds and blocks the function of tumor suppressor genes like the Retinoblastoma (Rb) and the Insulin-like Growth Factor Binding Protein-3" (IGFBP-3) through the Cys 24 and the C-terminal domain respectively (Nevins J R, 1992, Science 258:424-429) (Zwerschke W and Jansen-Durr P, 2000, Advances in Cancer Res 78:1-29). Similarly, the Ser 31/Ser 32 doublets in E7 protein have shown to be substrate for the CKII enzyme (Hashida T, Yasumoto S, 1990, Biochem. Biophys Res. Comm 172:958-964) and this domain is essential for both the transformant capacity of this oncoprotein (Barbosa M S, Edmonds C, Fisher C, Schiller J T, Lowy D R, Vousden K, 1990, EMBO J 9:153-160) (Chien W-M, Parker J N, Schmidt-Grimminger D-C, Broker T R, Chow L T, 2000, Cell Growth & Differentiation 11:425-435) and the inhibition of the IFN signaling cascade (Perea S E, López-Ocejo O, García Milián R, Banks L, Araña M J, 1996, Eur. Cytokine Net 7:503).

Based on the role of the CKII phosphorylation site in the HPV-resistance to IFN and cancer development, the designing of drugs blocking such a domain could become as useful tools for cancer therapy. Molecules inhibiting the CKII phosphorylation site either on E7 or in other cell substrates have not been described so far.

Concerning the E7 oncoprotein, only peptides blocking the Rb binding site (Cys 24) (Webster K R, Koleman K G, 1997, U.S. Pat. No. 5,625,031) (Oliff A I, Riemen M W, EP 0412762 A2 910213) and other C-terminal regions (39-98) have been described (Pidder J-D, Zwerschke W, 2000, EP0969013).

Some vaccine candidates focused to develop HPV E7-specific CTL response have been so far described in clinical or pre-clinical trials (Chen C, Wang C C, Hung C, Pardoll D M, Wu T, 2000, Vaccine 18:2015-2022) (Chen C H, Ji H, Suh K W, Choti M A, Pardoll D M, Wu T C, 1999, Gene Ther 12:1972-1981). However, the approaches focused to the CTL response face different obstacles related to the HPV biology. For instant, HPV oncogenic types down-regulate the MHC class I antigens which are essential for the CTL response (Connor M E, Stern P L, 1990, Int J Cancer 46:1029-1034). Furthermore, E7 expression has been associated with local immunosuppression at the tumor environment and this could also affect the appropriated development of the CTL response (Le Buanec H, D'Anna R, Lachgar A, Zagury J F, Bernard J, Ittlele D, d'Alessio P, Hallez S, Giannouli C, Burny A, Bizzini B, Gallo R C, Zagury D, 1999, Biomed Pharmacother 53:424-431) (Lee S J, Cho Y S, Shim J H, Lee K A, Ko K K, Choe Y K, Park S N, Hoshino T, Kim S, Dinarello C A, Yoon D Y, 2001, J Immunol 167:497-504). According to the above elements, it seems that combining CTL vaccines and pharmaceuticals targeting E7, could be of great perspectives.

Likewise, the approach of preventive HPV-vaccines faces a high benefit and cost risk due to different biological and social aspects including: 1) Long latency period after the HPV primary infection, 2) poor understanding of the HPV infection mechanism, 3) no animal model for the appropriated HPV propagation, 4) specie specificity and 5) the evaluation of the social impact of a preventive HPV vaccine could take quite long. Therefore, the using of pharmaceuticals specifically targeting viral oncoproteins could provide advantages over those approaches focused to the manipulation of the immune system.

ESSENCE OF THE INVENTION

The essence and novelty of this invention lies on the description for the first time of cyclic peptides allowing the direct inhibition of the CKII phosphorylation site as well as the cytotoxicity produced in vivo on HPV-16 cervical carcinoma cells. Furthermore, these peptides increase the sensitivity of the cells to the cytostatic effect of IFN.

DETAILED DESCRIPTION OF THE INVENTION

The invention is mainly referred to peptides able to bind the CKII phosphorylation site which exhibits the following sequences:

(a) CSVRQGPVQKC     (SEQ. ID. NO. 1)

(b) CSSCQNSPALC     (SEQ. ID. NO. 2)

(c) CQIPQRTATRC     (SEQ. ID. NO. 3)

(d) CAKQRTDPGYC     (SEQ. ID. NO. 4)

(e) CWMSPRHLGTC     (SEQ. ID. NO. 5)

(f) CRNCTVIQFSC     (SEQ. ID. NO. 6)

(g) CHYIAGTVQGC     (SEQ. ID. NO. 7)

(h) CPLVSLRDHSC     (SEQ. ID. NO. 8)

(i) CKQSYLHHLLC     (SEQ. ID. NO. 9)

(j) CFQPLTPLCRC     (SEQ. ID. NO. 10)

(k) CQSYHELLLQC     (SEQ. ID. NO. 11)

The invention also includes any homologue variant or mimetic from the peptides mentioned, that has been obtained by synthesis or recombinant way, as well as any fusion peptide containing the peptides described in the list. Any peptide, whose structure permits to block the CKII phosphorylation site in their respective substrates, is assumed as homologue variant. Likewise, any chemical molecule (no peptidic) whose structure permits to block such a phosphorylation site, is assumed as a mimetic variant.

Computer-simulated docking analysis of the Casein Kinase II (CKII) phosphorylation site revealed that a surprisingly large number of structurally related peptides are capable of inhibiting the CKII phosphorylation site. It was found that many cyclic peptides having a sequence related to one of peptides from "a" to "k" (SEQ ID NO: 1-11), having at least two cysteines that are engaged in a disulfide (S—S) bridge to provide the cyclic peptide structure, are capable of blocking the CKII phosphorylation site.

In one embodiment, the cyclic peptide has at least 10%, 20%, 30%, 40%, 50%, 60%, 70%, 80%, 90%, or 100% sequence identity with an amino acid sequence set forth in SEQ ID NOs: 1-11. In a preferred embodiment, the cyclic peptide has a total of eleven amino acid residues, nine of which are between two cysteine amino acid residues.

In another embodiment, the cyclic peptide includes a total of amino acid residues ranging from 9 to 30 amino acids between the two cysteines ($C_1$ and $C_2$). The two cysteine residues are engaged in the S—S bridge. The cyclic peptide further includes an aromatic amino acid residue (Ar) and a hydrophobic amino acid residue (Hy) separated by any sequence of five amino acid residues. Accordingly the cyclic peptide of the present embodiment is represented by the following motif: $C_1X_n\text{ArXXXXXHyX}_mC_2$, wherein X is any amino acid residue, n and m are integers selected from, and including, 0 to 23, and n+m is between 2 and 23. The cyclic peptide is capable of binding and inhibiting the CKII phosphorylation site as defined herein (See Examples 7 and 8).

The aromatic amino acid residue can be any one of the following: Phe (F) Tyr (Y) Trp (W) His (H). Most preferably, the aromatic amino acid residue Ar is a tryptophan (W) residue.

The hydrophobic amino acid can be any one of the following: Met (M) Leu (L) Ile (I) Val (V). Most preferably the hydrophobic amino acid residue (Hy) is a leucine (L) residue.

Thus, in most preferred embodiments, the homologue variant is a cyclic peptide having a total number of amino acid residues ranging from 11 and 32 amino acids, comprising two cysteine residues engaged in an S—S bridge and comprising the motif: $C_1X_nWXXXXXLX_mC_2$.

The peptide can include any combination of an aromatic amino acid residue in the Ar position and a hydrophobic amino acid residue in the Hy position. In one embodiment, the Ar is His (H) and the Hy is Val (V), $C_1X_nHXXXXXVX_mC_2$. An example of such a sequence is CHYIAGTVQGC (SEQ ID NO: 7), In another embodiment, the Ar is Phe (F) and the Hy is Leu (L), $C_1X_nFXXXXXLX_mC_2$. An example of such a sequence is CFQPLTPLCRC (SEQ ID NO: 10).

Especially preferred homologue variants are cyclic peptides having the sequence $C_1X_nWXXXXXLX_mC_2$, wherein X is any amino acid residue, n and m are integers selected from, and including, 0 to 23, and n+m is between 2 and 23), wherein the cysteine residues are linked by an S—S bridge.

Even more preferred homologue variants are cyclic peptides having the sequence $C_1X_nArXXXXXHyX_mC_2$, as described above, wherein the sequence XXXXX between the aromatic and hydrophobic residues has at least 20% sequence identity, preferably at least 40% sequence identity, more preferably at least 60% sequence identity, still more preferably at least 80% sequence identity, and most preferably at least 100% sequence identity with the sequence MSPRH (SEQ ID NO: 15).

As stated above, the sequence XXXXX between the aromatic and hydrophobic amino acid residues is a five amino-acid sequence in which X is any amino acid residue. In one embodiment, the sequence XXXXX between the aromatic and hydrophobic amino acid residues has at least 20% sequence identity, preferably at least 40% sequence identity, more preferably at least 60% sequence identity, still more preferably at least 80% sequence identity, and most preferably at least 100% sequence identity with the sequence YIAGT (SEQ ID NO: 16).

In another embodiment, the sequence XXXXX between the aromatic and hydrophobic amino acid residues has at least 20% sequence identity, preferably at least 40% sequence identity, more preferably at least 60% sequence identity, still more preferably at least 80% sequence identity, and most preferably at least 100% sequence identity with the sequence QPLTP (SEQ ID NO: 17).

Percent sequence identity is calculated as the percent nucleotides that are identical in two sequences being compared. To determine the percent identity of two amino acid sequences, the sequences are aligned for optimal comparison purposes.

For example, the determination of identity (percent) for the sequence XXXXX can be carried out as follows: I=(n÷5)×100, wherein/is the identity in percent and n is the number of identical nucleotides between the isolated nucleic acid molecule and the comparative sequence. The comparative sequence can include: MSPRH (SEQ ID NO: 15), YIAGT (SEQ ID NO: 16), or QPLTP (SEQ ID NO: 17).

Suitable substitution variants of the peptides include conservative amino acid substitutions. Conservative substitution tables providing functionally similar amino acids are well known in the art. Amino acids may be grouped according to their physicochemical characteristics. The following seven groups each contain amino acids that are conservative substitutions for one another:

(a) Small Non-polar amino acids: Ala (A) Ser (S) Thr (T) Pro (P) Gly (G);
(b) Acidic amino acids: Asn (N) Asp (D) Glu (E) Gln (Q);
(c) Basic amino acids: His (H) ArgI Lys (K);
(d) Hydrophobic amino acids: Met (M) Leu (L) Ile (I) Val (V)
(e) Aromatic amino acids: Phe (F) Tyr (Y) Trp (W) His (H)
(f) Sulfur-containing: Met (M), Cys I; and
(g) Aliphatic: Gly (G), Ala (A), Val (V), Leu (L), Ile (I).

Substitutions of an amino acid in a peptide by another amino acid in the same group is referred to as a conservative substitution and may preserve the physicochemical characteristics of the original peptide. Accordingly, unless otherwise indicated, a particular amino acid sequence can encompass conservative substitution variants thereof. For example, a conservative substitution of the sequence MSPRH (SEQ ID NO: 15) can include LSPRH (SEQ ID NO: 18), in which the Met (M) in the first residue position can be substituted for another hydrophobic amino acid, e.g., Leu (L). Further examples of a sequence XXXXX can include any one of the following sequences:

```
MSPRH          (SEQ ID NO: 15)
LSPRH          (SEQ ID NO: 18)
ISPRH          (SEQ ID NO: 19)
VSPRH          (SEQ ID NO: 20)
CSPRH          (SEQ ID NO: 21)
MAPRH          (SEQ ID NO: 22)
MTPRH          (SEQ ID NO: 23)
MPPRH          (SEQ ID NO: 24)
MGPRH          (SEQ ID NO: 25)
MSARH          (SEQ ID NO: 26)
MSSRH          (SEQ ID NO: 27)
MSTRH          (SEQ ID NO: 28)
MSGRH          (SEQ ID NO: 29)
MSPHH          (SEQ ID NO: 30)
MSPKH          (SEQ ID NO: 31)
MSPRF          (SEQ ID NO: 32)
MSPRY          (SEQ ID NO: 33)
MSPRW          (SEQ ID NO: 34)
```

In addition, suitable substitution variants of the peptides include substitutions for a non-polar amino acid. For example, a non-polar amino acid substitution of the sequence MSPRH (SEQ ID NO: 15) can include SSPRH (SEQ ID NO: 68), in which the Met (M) in the first residue position can be substituted for the non-polar amino acid Ser (S).

The sequences for $X_n$ and $X_m$ are not particularly limiting. $X_n$ and $X_m$ can include any amino acid sequence. For example, $X_n$ can be AG, AA, AS, AT, AP, AG, SA, SS, ST, SP, SG, TA, TS, TP, TG, PA, PS, PT, PP, PG, GA, GS, GT, GP, or GG. Preferably, $X_n$ is AG. For example, $X_m$ can be GT, QG, CR, QK, AL, TR, GY, FS, HS, LL, or LQ.

In the event that n is 0 and m is 2, and $X_m$ denotes the amino acids GT, the $C_1X_nWXXXXXLX_mC_2$ sequence would correspond to SEQ ID NO:5 (or peptide "e") as disclosed herein.

In another embodiment, n is 0 and m is 2, and $X_m$ denotes the amino acids QG, the sequence XXXXX is YIAGT (SEQ ID NO: 16), then the $C_1X_nHXXXXXVX_mC_2$ sequence would correspond to SEQ ID NO: 7 (or peptide "g") as disclosed herein.

In a further embodiment, n is 0 and m is 2, and $X_m$ denotes the amino acids CR, the sequence XXXXX is QPLTP (SEQ ID NO: 17), then the $C_1X_nFXXXXXLX_mC_2$ sequence would correspond to SEQ ID NO: 10 (or peptide "j") as disclosed herein.

Preferably the sequence $X_m$ refers to an amino acid sequence GTASAAGAAGGAYAAGSHIGA (SEQ ID NO: 35) or a sequence having at least 2, more preferably at least 3, 4, 5, 6, 7, 8, 9, 10, 11, 12, 13, 14, 15, 16, 17, 18, 19, more preferably 20 sequential amino acids starting from the N-terminal part of sequence GTASAAGAAGGAYAAGSHIGA (SEQ ID NO: 35). For example, a sequence $X_m$ can include any one of the following sequences:

```
GTASAAGAAGGAYAAGSHIGA    (SEQ ID NO: 35)
GTASAAGAAGGAYAAGSHIG     (SEQ ID NO: 36)
GTASAAGAAGGAYAAGSHIC     (SEQ ID NO: 37)
GTASAAGAAGGAYAAGSHI      (SEQ ID NO: 38)
GTASAAGAAGGAYAAGSH       (SEQ ID NO: 39)
GTASAAGAAGGAYAAGS        (SEQ ID NO: 40)
GTASAAGAAGGAYAAG         (SEQ ID NO: 41)
GTASAAGAAGGAYAA          (SEQ ID NO: 42)
GTASAAGAAGGAYA           (SEQ ID NO: 43)
GTASAAGAAGGAY            (SEQ ID NO: 44)
GTASAAGAAGGA             (SEQ ID NO: 45)
GTASAAGAAGG              (SEQ ID NO: 46)
GTASAAGAAG               (SEQ ID NO: 47)
GTASAAGAA                (SEQ ID NO: 48)
GTASAAGA                 (SEQ ID NO: 49)
GTASAAG                  (SEQ ID NO: 50)
GTASAA                   (SEQ ID NO: 51)
GTASA                    (SEQ ID NO: 52)
GTAS                     (SEQ ID NO: 53)
GTA
GT
```

Even more preferably, the sequence $X_m$ refers to an amino acid sequence having at least 5, 10, 15, 20, 25, 30, 35, 40, 45, 50, 55, 60, 65, 70, 75, 80, 85, 90, or 95% sequence identity to the amino acid sequence GTASAAGAAGGAYAAGSHIGA (SEQ ID NO: 35) or an N-terminal part thereof. Preferably the sequence $X_n$ refers to an amino acid sequence AG, or a conservative amino acid substitution thereof.

Other object of the invention is the pharmaceutical composition which comprises one or more of the peptides described in the invention as well as an appropriated carrier.

Likewise, the invention comprises the use of the mentioned peptides alone or combined with any other appropriated molecule as cytokines and interferons to: 1) inhibit the proliferation of tumor cells, 2) treating both HPV-associated and not associated cancer and 3) treating HPV-associated lesions at the pre-malignant stages.

Furthermore, the peptides of the invention could be employed for treating HPV-infected patients resistant toward interferon treatment.

In other respect of the invention, it comprises one expression vector for mammalian cells containing a DNA sequence which codes for any of the peptides above referred.

The peptides of the invention have a cyclic structure and they are mainly characterized by the ability to bind the CKII phosphorylation site and abrogate such biochemical event. The peptides are described on the list enclosed. On the other hand, the in vivo effects produced by the peptides on HPV-16 transformed cells are also shown.

The peptides described were defined by their ability of both inhibiting the phosphorylation of the sequence RRREEE-TEEE (SEQ. ID. NO. 12) previously reported as the optimal consensus domain for the CKII phosphorylation (Promega Cat:V5661) and the phosphorylation site contained in the region 28-38 of the HPV-16 E7 oncoprotein.

To define the peptides described in the invention, one 11-aminoacid cyclic peptide library was constructed and expressed on the P8 region from filamentous phages. The screening of the library was performed using the synthetic 28-38 region of E7 as target, which was also conjugated to biotin for fixing it to a solid surface. Selection of those phages bound to the 28-38 region of E7 was carried out by immunodetection using an specific antibody against the P8 region in the phage. Finally, DNA corresponding to the eleven phages with high capacity of binding to the 28-38 region of E7, was sequenced and the respective peptides were chemically synthesized by the solid phase method. The synthetic peptides were further purified by HPLC, analyzed by mass spectrometry and finally evaluated respecting the in vitro and in vivo efficacy.

According to this invention, in spite of the different aminoacid sequences among the cyclic peptides described here, they equally inhibit the CKII phosphorylation event. This fact denotes that the interaction of these peptides with the CKII phosphorylation site is mainly based on their structure rather than the sequence itself.

In this invention, it is also demonstrated that lineal peptides exhibit a lower capacity of inhibiting the CKII phosphorylation site. This finding reinforces the importance of structure in the binding capacity of these peptides to such a domain. Also, this finding suggests the efficacy of other mimetic molecules, which bind to the CKII phosphorylation site.

In order to achieve the intracellular action on the CKII endogenous substrates, the described peptides can be chemically conjugated or genetically fused to the cell penetrating peptides belonging to proteins like the Human Immunodeficiency Virus (HIV-1) Tat 1 (Schwarze S R, Dowdy S F, 2000, Trends Pharmacol 21:45-48), the transcription factor coded by the Drosophyla Antenapedia gene (Derossi D, et al, 1996, J. Biol Chem 271:18188-18193), the Herpes Simplex Virus (HSV) VP22 protein (Lindgreen M, et al., 2000, Trends Pharmacol Sci 21:99-103), the penetratin and transportan (Gariepy J, Kawamura K, 2001, Trends Biotech 19:21-28) among others. To test the in vivo hypothesis in this invention, the cyclic peptides were synthesized fused to the cell penetrating peptide reported for the HIV-1 Tat 1 protein (GRKKRRQR- RRPPQC (SEQ. ID. NO. 13)) and one nuclear localization signal belonging to the SV 40 T large antigen (KKKRKVE SEQ. ID. NO. 14)).

Data shown in this invention clearly indicate that cyclic peptides exhibit cytotoxicity in a dose-dependent manner on cervical carcinoma cells transformed by HPV-16 (CaSki). These results suggest the employment of these peptides as a therapeutical tool for treating tumors from the same histologic origin as well as from premalignant stages like the cervical intraepithelial neoplasia. Likewise, the in vivo experimental data showed that cyclic peptides were more effective than their respective lineal form thus reinforcing the importance of structure on the effect itself.

Likewise, the cyclic peptides described in this invention are effective on Hela cells containing the HPV-18 as well as on H-82 cells derived from Non-Small Lung cell cancer negative for HPV. These results correlate to those obtained in vitro in this invention where peptides block nor only the CKII phosphorylation site on the HPV-16 E7 but also they block it in other proteins containing such a site. The fact that the peptides described here are effective on HPV-negative tumor cells provides an argument for its potential employment in other epithelial tumors.

Other results in this invention indicate that treatment of CaSKi cells with the cyclic peptides described here increases the cell sensitivity to the cytostatic effect of IFN alpha. Considering previous evidences showing that the CKII phosphorylation site on the HPV-16 E7 is required for blocking the IFN signaling cascade (Perea S E, López-Ocejo O, García Milián R, Banks L, Araña M J, 1996, Eur. Cytokine Net 7:503), the peptides described here can be useful in bypassing the common IFN-resistance observed on HPV infection.

The object of this invention can be also related to the DNA coding for each peptide described here. This DNA could be introduced in a mammalian expression vector and further transfected into both HPV-16-transformed and -no transformed cells. The vector containing the oligonucleotide that codes for each peptide can be also used as an alternative for the gene therapy in HPV-associated cancer.

In principle, the peptides described here can be used in HPV-associated diseases along with other agents as well as with therapeutic vaccines based cellular response against HPV.

This invention is illustrated by the following examples:

Example 1

Effect of the Peptides on the CKII Phosphorylation Site

This assay is based on an in vitro phosphorylation reaction using the substrate sequence RRREEETEEE which represents the optimized consensus domain for the CKII phosphorylation. The reaction is performed in 50 µl of Tris:HCL 25 mM pH 7.5, 1 µCi $^{32}$P-γATP, 100 µM ATP, 2 mg/ml of the substrate peptide, 0.2 M NaCl, 10 mM MgCl and 1 unit of the CKII enzyme (Promega). Reaction is incubated at 37° C. during 10 minutes. Afterward, 5 µl of reaction were spotted onto PE-81 chromatography paper (Whatmann) and four washes with 10 mM $H_3PO_4$ were made. Finally, the radioactivity associated to the filters was measured and the cpm levels show the CKII enzymatic activity in each sample. Simultaneously, an specific CKII inhibitor like heparin is included in the assay as an internal control. Data show in the FIG. 1 demonstrated that cyclic peptides inhibit the CKII phosphorylation by 80%. Also, lineal peptides inhibit the CKII phosphorylation of the 28-38 region on E7 although to a lesser extent compared with cyclic form. These evidences indicate that the peptides described here inhibit the CKII phosphorylation site and suggest that structure plays an essential role on their interaction with the target sequences.

Example 2

Effect of the Peptides on the HPV-16 E7 Phosphorylation

This assay is based on the in vitro phosphorylation reaction of the HPV-16 E7 oncoprotein expressed in E. Coli as a fusion protein to the Glutathione S Transferase (GST). Before enzymatic reaction, the E7-GST fusion protein was purified by affinity chromatography using Glutathione Sepharose beads (Pharmacia). The mixture reaction is performed in 50 µl de buffer Tris:HCL 25 mM pH 7.5, 1 µCi de $^{32}$P-γATP, 100 µM ATP, 40 µl of the beads containing E7-GST, 0.2 M NaCl, 10 mM MgCl and 1 unit of CKII (Promega). The reaction is incubated at 37° C. during 40 min. Afterward, the beads are washed away three times with 0.5 ml of the buffer and finally the phosphorylation level of the E7-GST is analyzed by 10% SDS-PAGE electrophoresis. The visualization of the phosphorylated proteins was performed by developing X-Rays films previously exposed to the dried gels. The quantification of the E7 phosphorylation was made by densitometry. Data in FIG. 2 indicate that the peptides described here are equally effective in terms of the inhibition of the CKII phosphorylation site on the HPV-16 E7.

Example 3

Effect of the Peptides on the Proliferation of HPV-16 and HPV-18-Transformed Cells (CaSki and HeLa Respectively)

In this assay, CaSki or HeLa cells were seeded at 2×10$^4$ cells/ml in 96-well plates (Costar) using DMEM supplied with 10% of Fetal Calf Serum (FCS) (Gibco). After 24 hours, peptides were added to the culture medium at doses comprising a range between 15 µM and 500 µM. The incubation was performed during 96 hours in 5% $CO_2$ and finally 20 µl of a MTS solution (1.90 mg/ml) Promega were added to each well. Plates were subsequently maintained one hour at the same incubation conditions and the absorbance at 490 nm was finally analyzed. Results are expressed as percent of growth respect the control without peptides. For this purpose, both cyclic and lineal peptides were chemically synthesized fused to the HIV-1 Tat-1 cell penetrating peptide which is able to penetrate into cytoplasm and nucleus (Schwarze S R, Dowdy S F, 2000. Trends Pharmacol 21:45-48). Data obtained from this experiment demonstrated that peptides described here produce a dose-dependent effect both on CaSki (HPV-16) and HeLa (HPV-18) cells (FIGS. 3 A and 3 B). This example shows that peptides from this invention are effective nor only for HPV-16 but also for HPV-18.

Example 4

Effect of the Peptides on the Proliferation of HPV-Negative Tumor Cells

In this assay, H-82 cells (Small Lung Cells Cancer) were seeded at 2×10$^4$ cells/ml in 96-well plates (Costar) using DMEM supplied with 10% of Fetal Calf Serum (FCS) (Gibco). After 24 hours, peptides were added to the culture medium at doses comprising a range between 15 µM and 500

μM. The incubation was performed during 96 hours in 5% $CO_2$ and finally 20 μl of a MTS solution (1.90 mg/ml) Promega were added to each well. Plates were subsequently maintained one hour at the same incubation conditions and the absorbance at 490 nm was finally analyzed. Results are expressed as percent of growth respect the control without peptides. For this assay, the cyclic peptides described in the invention fused to the HIV-1 Tat-1 cell penetrating peptide were employed as referred above. Results obtained from this experiments demonstrated that peptides from this invention produce a dose-dependent effect on the cell proliferation of H-82 cells. In FIG. 4 it is demonstrated that peptides from the invention are effective nor only for HPV-transformed cells but also for tumor cells from other localization and histological types like Small Lung Cell Cancer.

Example 5

Effect of the Peptides on the HPV-16 Response Toward IFN Treatment in CaSki Cells In this assay, CaSki cells were seeded at $2 \times 10^4$ cells/ml in 96-well plates (Costar) using DMEM supplemented with 10% FCS (Gibco). After 24 hours, 120 μM of each peptide were added to the culture medium. Twenty four hours later, alpha IFN was added in range between 1000 and 31.5 U/ml. The incubation was performed during 96 hours in 5% $CO_2$ and 20 μl of MTS 1.90 mg/ml were added afterward. Furthermore, plates were maintained one hour at the same conditions and the absorbance at 490 nm was finally read. Data are shown as percent of growth respect to the control. In these experiments, the peptides described in the invention were used in their cyclic variant fused to the cell penetrating peptide belonging the HIV Tat-1 protein as mentioned above. Results observed in the FIG. 5 demonstrate that previous incubation of CaSki cells with the peptides described in the invention makes these cells sensitive to the antiproliferative effect of alpha IFN. These data suggest the utility of the peptides described in the invention for treating HPV-infected patients who are refractory to the IFN therapy.

Example 6

Antitumor Effect of the CKII Phosphorylation Inhibitory Peptide in Human Tumors Implanted in Nude Mice Models For these experiments, 6-8 week old female BalbC nude mice were used. The tumor implantation was performed using H-125 cells (Non-Small Lung Cell Cancer) that were resuspended in saline solution (PBS) at 1000 000 cells/ml. Cell suspension was inoculated subcutaneously in the abdomen. Peptide administration (sequence 1 on the list) was made together with the cells and continued every other day until completing one month of treatment. In this assay, doses ranging between 1 and 10 mg/Kg of weight were evaluated. To examine the antitumor effect, parameters like tumor mass and survival of the animals were evaluated. As observed in FIG. 6, the three peptide doses were effective in terms of the inhibition of tumor progression. These data show the antitumor efficacy of the CKII phosphorylation inhibitory peptide in a model of human tumor implanted in experimental animals.

Example 7

Studies on Homologous Variants Using a Structure-Function Analysis Approach on Peptide "e" (SEQ ID NO: 5)

Alanine Scanning Analysis

The biological activity of different homologue variants of one of the peptides described herein was examined. In particular, an alanine scanning analysis of the peptide herein referred to as peptide "e" and having the sequence of SEQ ID No. 5 (CWMSPRHLGTC) was performed.

The following peptide variant were synthesized for alanine scanning:

```
CWMSPRHLGTC
(peptide "e" having the sequence of SEQ ID No. 5)
(wild-type, also termed F20-16)

CAMSPRHLGTC    (SEQ ID NO: 54)    (F21-40)

CWASPRHLGTC    (SEQ ID NO: 55)    (F21-41)

CWMAPRHLGTC    (SEQ ID NO: 56)    (F21-42)

CWMSARHLGTC    (SEQ ID NO: 57)    (F21-43)

CWMSPAHLGTC    (SEQ ID NO: 58)    (F21-44)

CWMSPRALGTC    (SEQ ID NO: 59)    (F21-45)

CWMSPRHAGTC    (SEQ ID NO: 60)    (F21-46)

CWMSPRHLATC    (SEQ ID NO: 61)    (F21-47)

CWMSPRHLGAC    (SEQ ID NO: 62)    (F21-48)
```

Each alanine mutant was synthetically fused to the Tat cell penetrating peptide for the biological assay and further cycled by the cysteine residues. For the experiment, human Non Small Cell Lung Cancer (NSCLC) H-125 cells were seeded at $2 \times 10^4$ cells/ml in 96-well plates (Costar) using DMEM supplemented with 10% FCS (Gibco). After 24 hours, peptides derived from the alanine scanning were added to the culture medium in a dose range from 0 to 200 μM. The incubation was performed during 72 hours at 37° C. in 5% $CO_2$, and finally 20 μl of MTS (1.90 mg/ml) were added to each well. Furthermore, plates were maintained one additional hour at the same conditions and the absorbance at 490 nm was taken in a multiscan reader (Amersham-Pharmacia).

Results are presented in FIG. 7 wherein the Inhibitory Concentration 50 (IC50) values are presented as obtained from the respective dose-response curves for each of the peptide variants. IC50 is defined herein as the concentration of each peptide which produces a 50% cell growth inhibition. As shown in FIG. 7, all of the variants containing single substitutions of alanine are able to inhibit cell proliferation to a similar extent as that observed for the wild-type peptide having the sequence as provided in SEQ ID NO:5. Interestingly, those variants with substitutions on W and L (amino acid positions 2 and 8) exhibited higher IC50 levels on these cells. That is, both of these mutants inhibit the cell growth less efficiently. However, most of the variants of this peptide maintain the ability to inhibit tumor cell proliferation. Based on the results from the alanine scanning, the tryptophane (W) and leucine (L) residues, on positions 2 and 8, respectively, in the linear sequence annotation, are preferably present in a peptide of the invention as they provide for a high level inhibitory effect on tumor cells.

Example 8

Studies on Homologous Variants Using a Structure-Function Analysis Approach on Peptide "e" (SEQ ID NO: 5)

Effect of Peptide Length on Biological Activity

To explore the maximal peptide length necessary to retain the biological activity of the peptide "e" having the sequence of SEQ ID No. 5, and based on the strong homology conserved through the CK2 substrates, we performed a structural analysis using the Calmodulin protein as substrate. Data from such analysis indicated that homologue variants of the peptide "e" should not exceed the amount of 30 amino acids between the two Cysteines engaged in the S—S bridge. Therefore, different homologue variants were synthesized and the respective biological activity on tumor cells was tested.

The following synthetic homologues were synthesized:

```
                                              (SEQ ID NO: 5)
Peptide "e":    CWMSPRHLGTC
                (11 residues)

(SEQ ID NO: 63)
Hom-1:          CAGWMAPRHLGTASAAGAAGGAYAAGSHIGAC
                (32 residues)

(SEQ ID NO: 64)
Hom-2:          CAGWMAPRHLGTASAAGAAGGAYAAGSHIC
                (30 residues)

(SEQ ID NO: 65)
Hom-3:          CAGWMAPRHLGTASAAGAAGGAYAAGSHIGAAC
                (33 residues)

(SEQ ID NO: 66)
Hom-4:          CAGWMAPRHAGTASAAGAAGGAYAAGSHIGAC
                (32 residues)

(SEQ ID NO: 67)
Hom-5:          CAGAMAPRHLGTASAAGAAGGAYAAGSHIGAC
                (32 residues)
```

For testing the biological activity, each homologue variant was synthetically fused to the Tat cell penetrating peptide and further cycled by the cysteine residues. Briefly, Human Non Small Cell Lung Cancer (NSCLC) H-125 cells were seeded at $2 \times 10^4$ cells/ml in 96-well plates (Costar) using DMEM supplemented with 10% FCS (Gibco). After 24 hours, peptide variants were added to the culture medium in a dose range from 0 to 200 µM. The incubation was performed during 72 hours at 37° C. in 5% $CO_2$ and, finally, 20 µl of MTS (1.90 mg/ml) were added to each well. Furthermore, plates were maintained one additional hour at the same conditions and the absorbance at 490 nm was taken in a multiscan reader (Amersham-Pharmacia).

Results are presented in FIG. 8 wherein the Inhibitory Concentration 50 (IC50) values are presented as obtained from the respective dose-response curves for each of the peptide variants. As expected, the longer homologue versions of the peptide "e" also required the two amino acids W and L in order to provide for a high level inhibitory effect, as explained above and observed by Alanine scanning. As shown in FIG. 8, the homologue variants containing up to 30 amino acids between the two cysteines engaged in the S—S bridge were biologically active on tumor cells (total length 32 residues). However, longer variants did not retain the biological function and the peptide became inactive. As expected, those variants with substitutions on W and L exhibited reduced biological activity on tumor cells.

Advantages of the Invention

1. Provides pharmaceuticals of wide application spectrum which are nor only useful in HPV-associated diseases but also in solid tumors with high levels of CKII endogenous activity.
2. The fact that the 28-38 region is conserved among HPVs, it provides the possibility of using this pharmaceutical in diseases associated to different HPV types.
3. Peptides as therapeutical molecules exhibit low antigenicity when administered to human beings.
4. Is a pharmaceutical of easy manufacturing and low cost.

BRIEF DESCRIPTION OF FIGURES

FIG. 3 B: Effect of peptides on the proliferation of HeLa cells

INCORPORATION OF SEQUENCE LISTING

Figure 1:
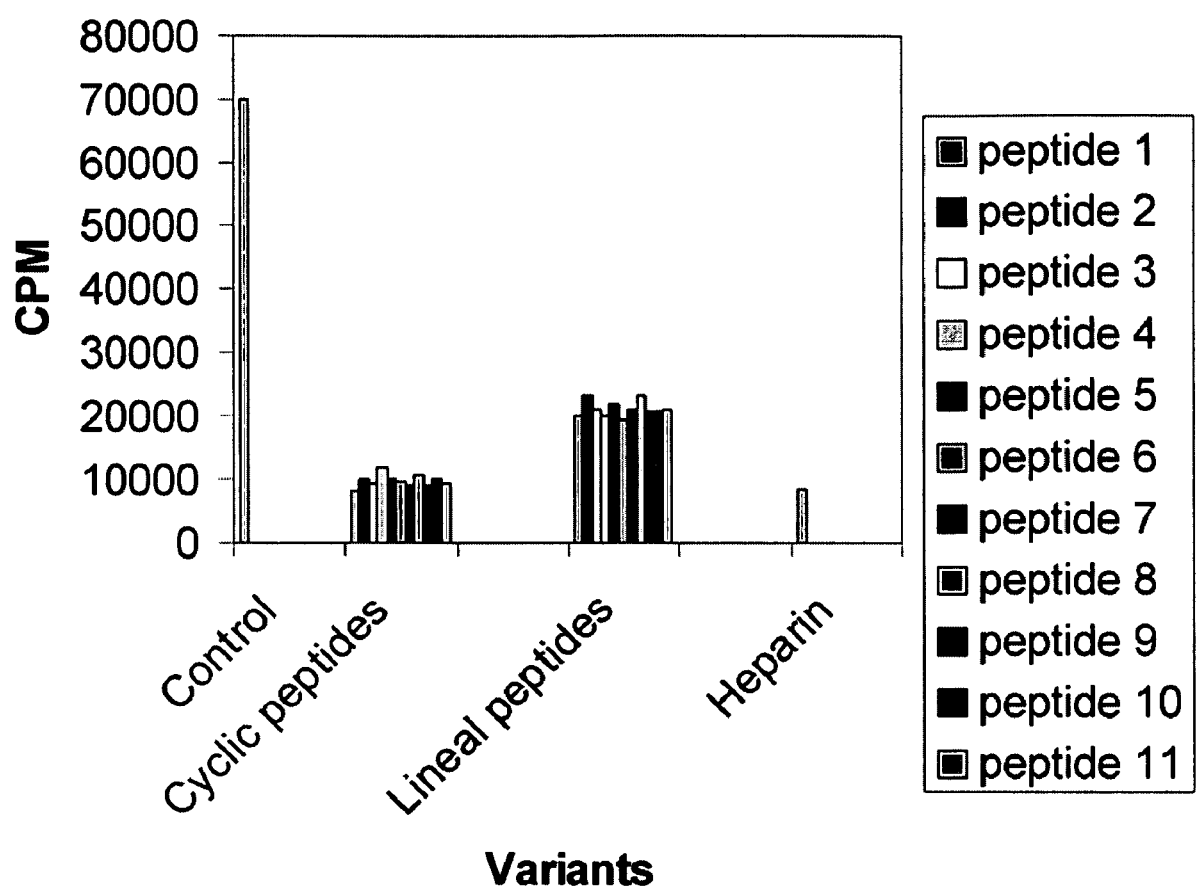
FIG. 1: Effect of peptides on the CKII phosphorylation
Figure 2:
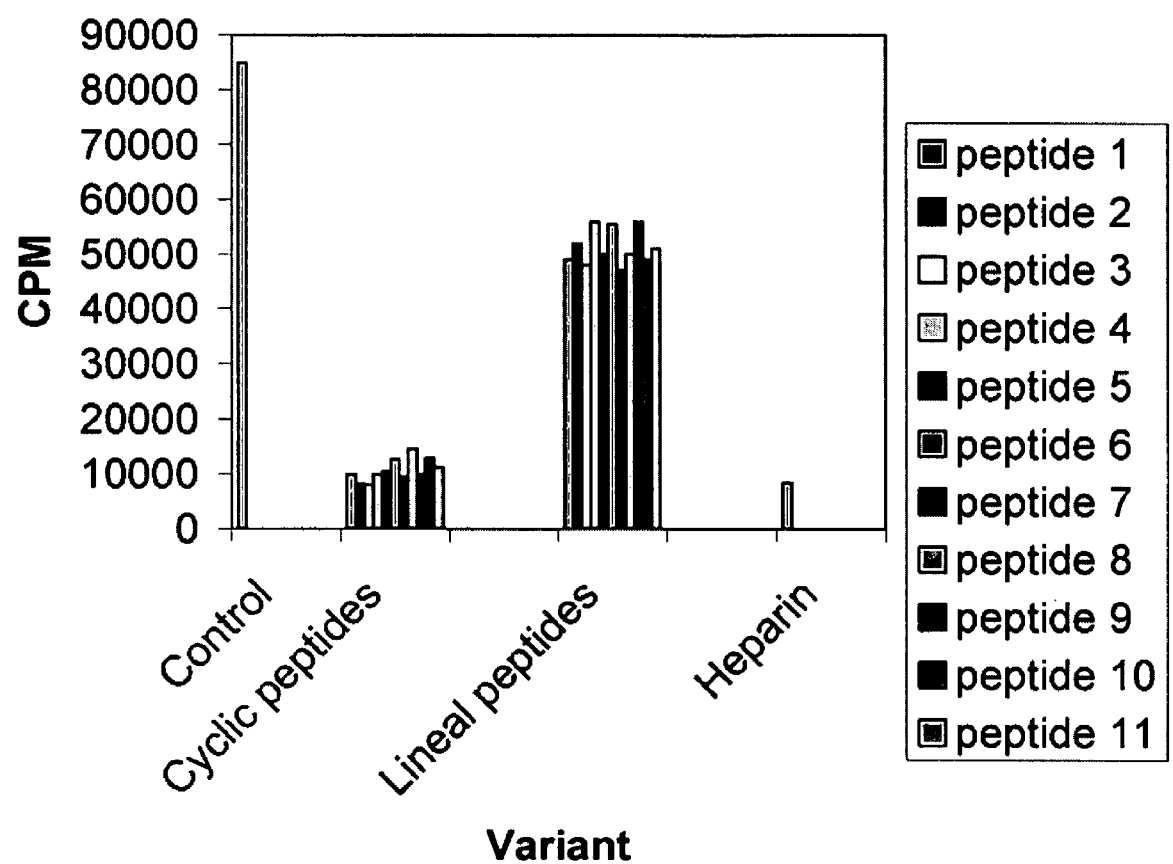
FIG. 2: Effect of peptides on the HPVE7 CKII phosphorylation
Figure 3A:
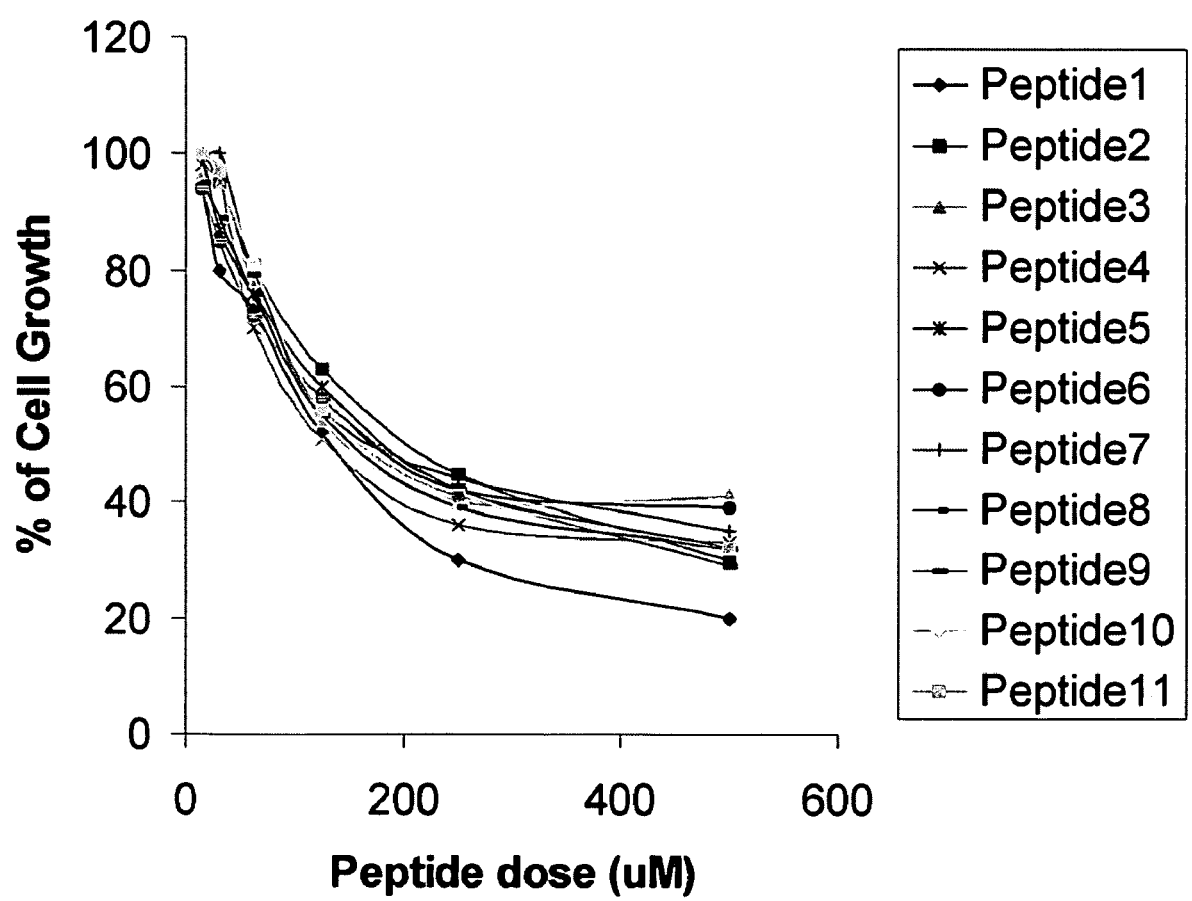
FIG. 3 A: Effect of peptides on the proliferation of CaSki cells
Figure 3B:
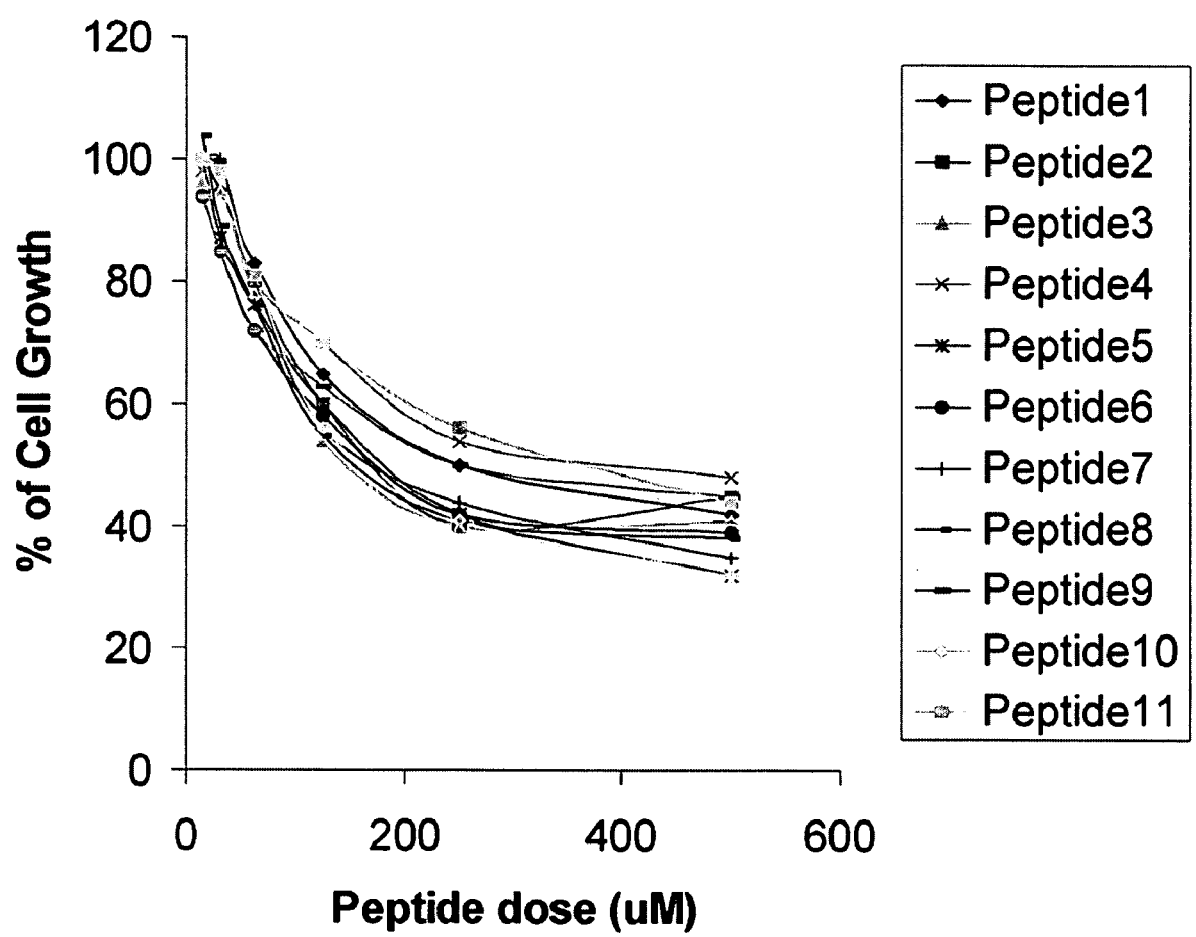
Figure 4:
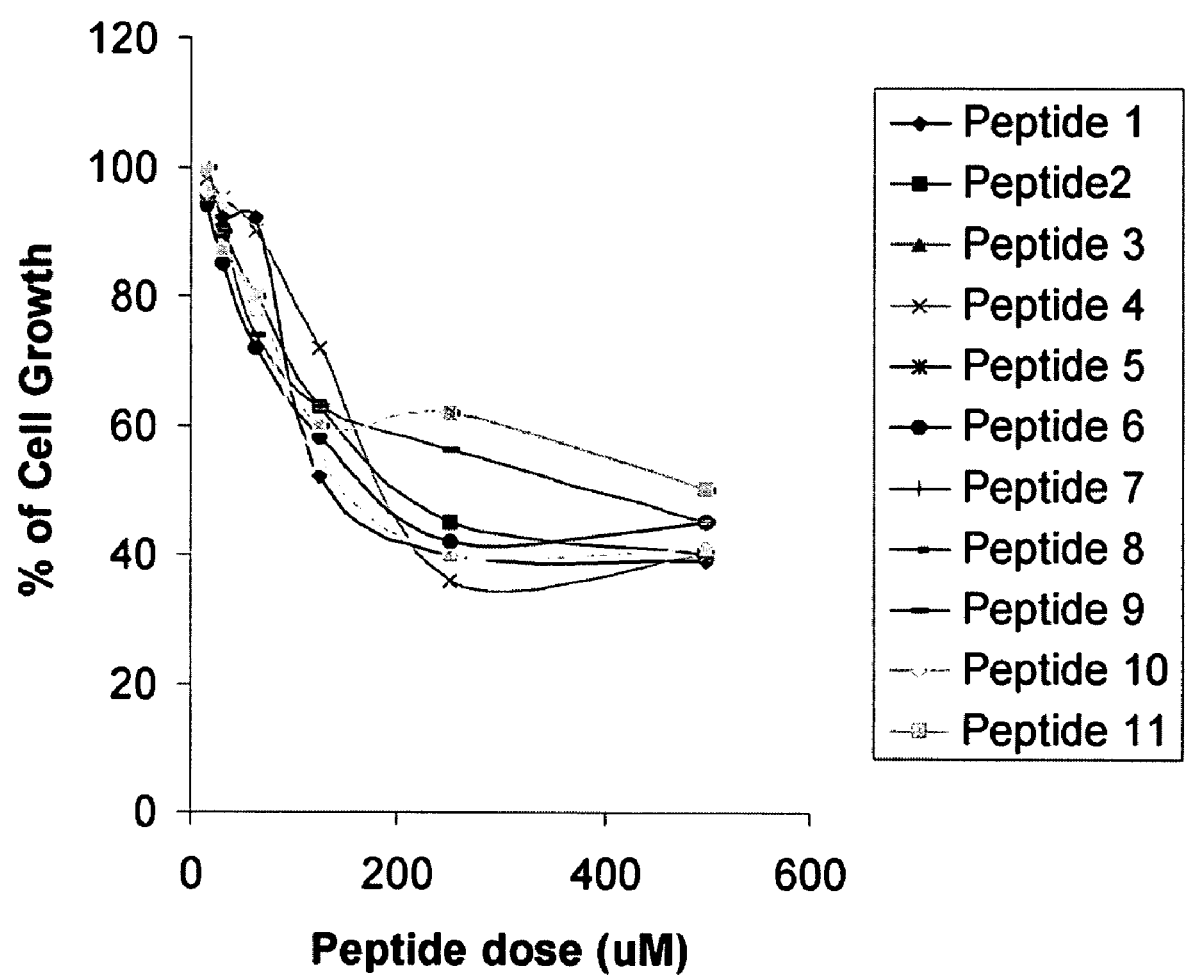
FIG. 4: Effect of peptides on the proliferation of Lung tumor cells
Figure 5:
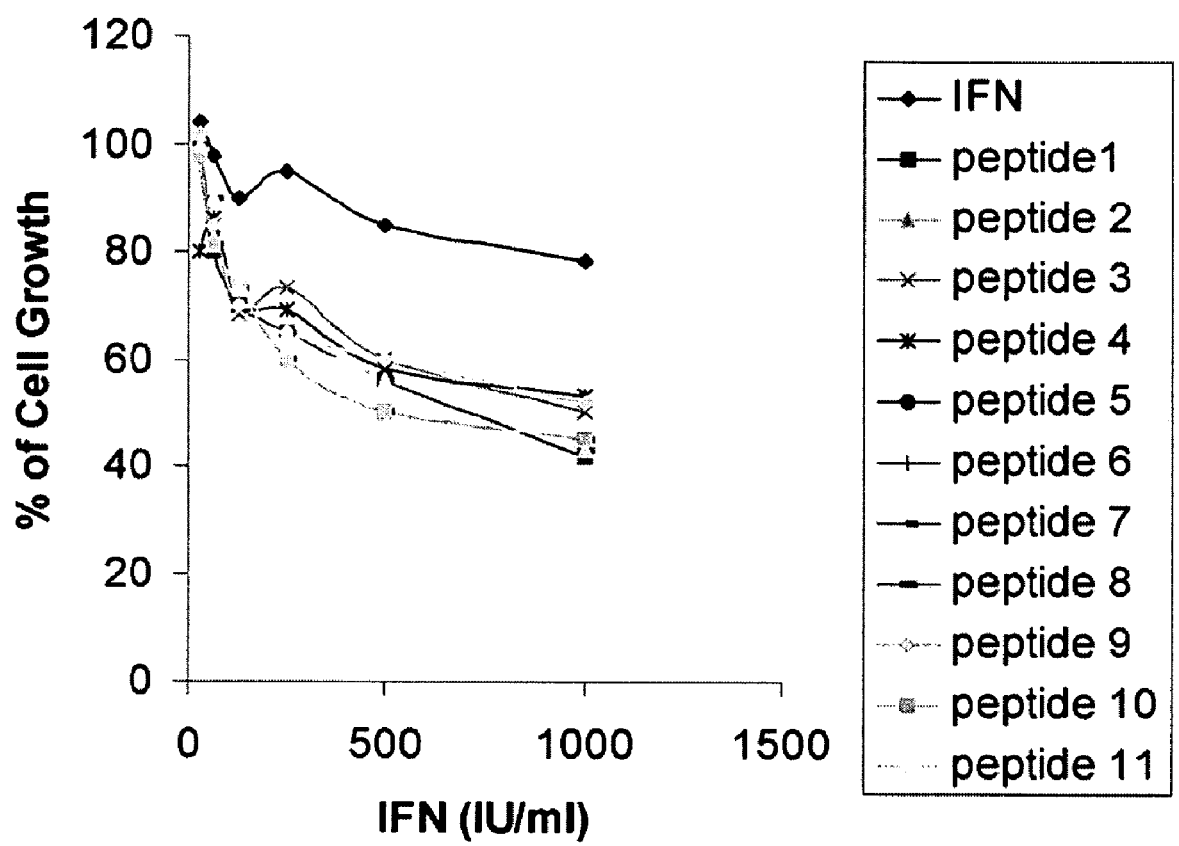
FIG. 5: Effect of peptides on the response of HPV-16 transformed cells toward IFN action
Figure 6:
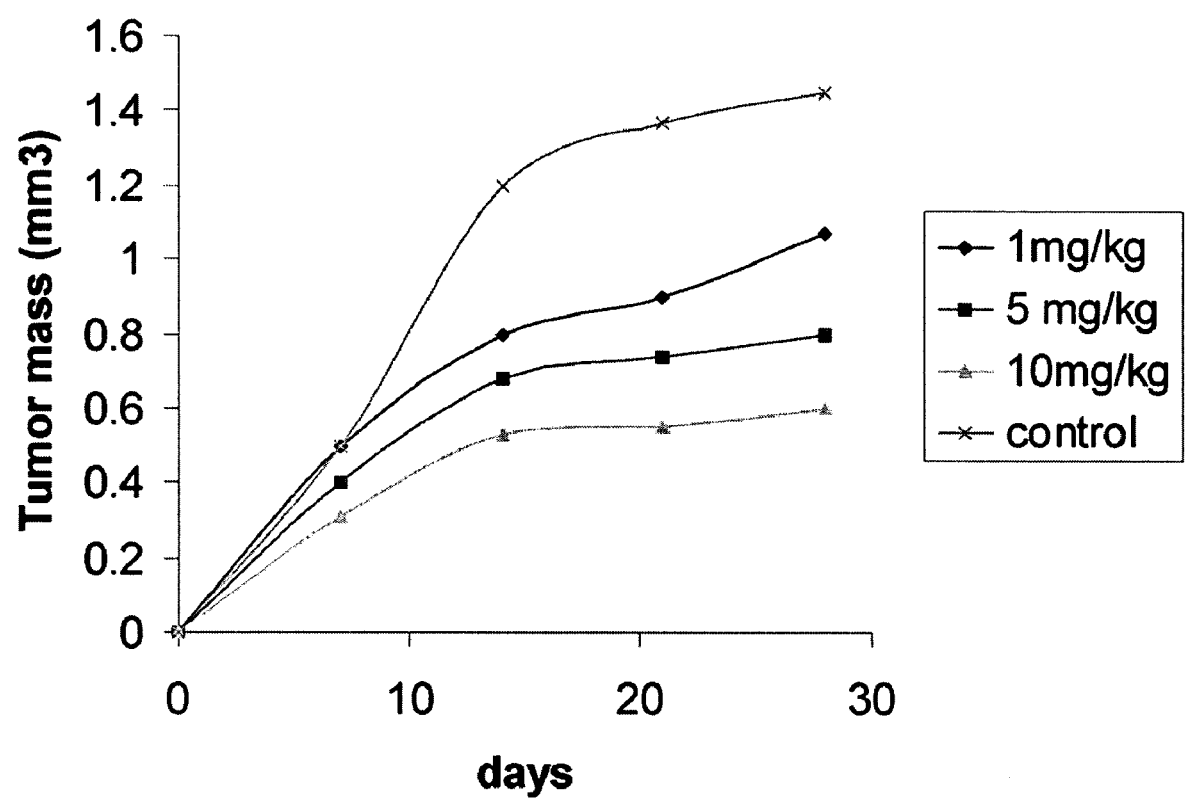
FIG. 6: Antitumor effect of the CKII phosphorylation inhibitory peptide in human tumors implanted in nude mice
Figure 7:
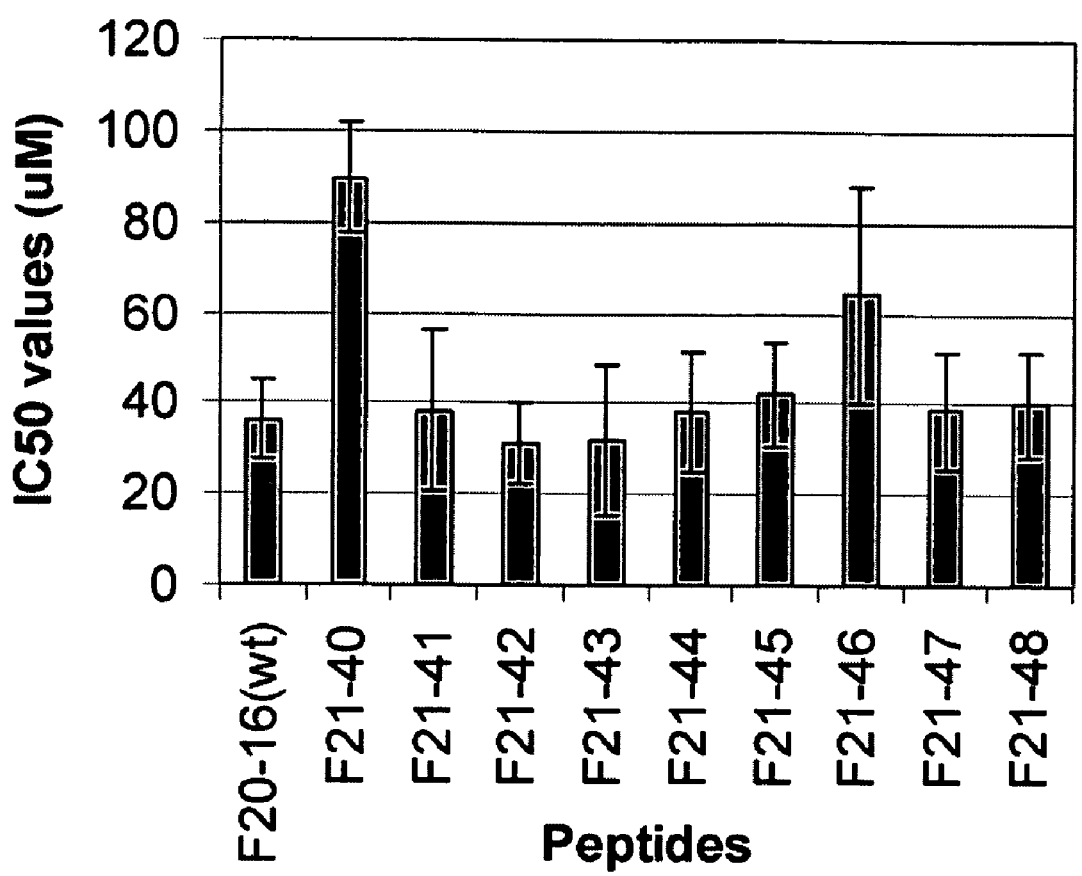
FIG. 7: Result of the structure-function analysis of the peptide described herein as SEQ ID No. 5. In essence, human lung cancer cells (H-125) were seeded at $2 \times 10^4$ cells/ml in 96-well plates. Each peptide derived from the alanine scanning from the peptide (SEQ ID No. 5, peptide "e") was synthetically fused to the Tat cell penetrating peptide and further cycled by the cysteine residues. The concentration of the different peptide homologues ranged from 0 to 200 µM and the antiproliferative effect in each case on NSCLC H-125 tumor cells is expressed as $IC_{50}$ values.
Figure 8:
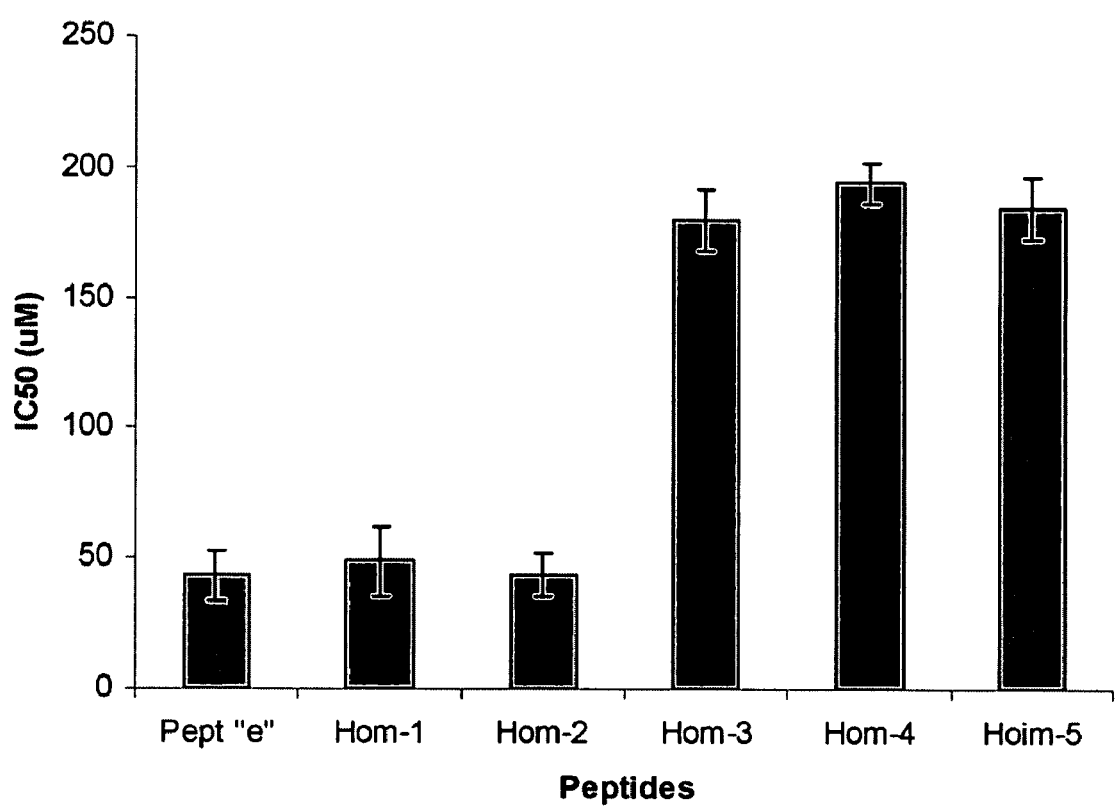
FIG. 8: Result of the effect of the peptide length on the biological activity of homologue variants. In essence, human lung cancer cells (H-125) were seeded at $2 \times 10^4$ cells/ml in 96-well plates. Each synthetic homologue peptide was synthetically fused to the Tat cell penetrating peptide and further cycled by the cysteine residues. The concentration of the different peptide variants ranged from 0 to 200 µM and the antiproliferative effect in each case is expressed as IC50 values.

Incorporated herein by reference in its entirety is the Sequence Listing for the application. The Sequence Listing is disclosed on a computer-readable ASCII text file titled, "sequence_listing.txt", created on Aug. 19, 2008. The sequence_listing.txt file is 14.6 kb in size.

The invention claimed is:

1. A cyclic peptide comprising an amino acid sequence having the sequence $C_1X_nArMSPRHHyX_mC_2$, wherein X is any amino acid residue;

n and m are integers selected from 0 to 23;

n+m is between 2 and 23;

Hy is a hydrophobic amino acid residue;

Ar is an aromatic amino acid residue; and wherein the cyclic peptide binds to and inhibits a Casein Kinase II (CKII) phosphorylation site.

2. The peptide according to claim 1, wherein the cyclic peptide has a total of eleven amino acid residues, wherein nine of the eleven amino acid residues are located between two cysteine amino acid residues linked by a disulfide bridge.

3. A cyclic peptide according to claim 1, having the sequence selected from the group consisting of SEQ ID NO: 5, SEQ ID NO: 54, SEQ ID NO: 60, SEQ ID NO:61 and SEQ ID NO: 62.

* * * * *